United States Patent
Tanga et al.

(10) Patent No.: US 7,022,473 B1
(45) Date of Patent: Apr. 4, 2006

(54) SUBSTRATES FOR IMMOBILIZING AND AMPLIFYING DNA AND DNA-IMMOBILIZED CHIPS

(75) Inventors: Michifumi Tanga, Yamaguchi-ken (JP); Kojiro Takahashi, Hiroshima-ken (JP)

(73) Assignee: Toyo Kohan Co., Ltd, Tokyo (JP)

( * ) Notice: Subject to any disclaimer, the term of this patent is extended or adjusted under 35 U.S.C. 154(b) by 0 days.

(21) Appl. No.: 09/601,875

(22) PCT Filed: Feb. 8, 1999

(86) PCT No.: PCT/JP99/00524

§ 371 (c)(1),
(2), (4) Date: Oct. 12, 2000

(87) PCT Pub. No.: WO99/40173

PCT Pub. Date: Aug. 12, 1999

(30) Foreign Application Priority Data

Feb. 9, 1998 (JP) ................................. 10/041035

(51) Int. Cl.
*C12Q 1/68* (2006.01)
*C12M 1/36* (2006.01)
*C07H 21/04* (2006.01)
*B01J 29/04* (2006.01)

(52) U.S. Cl. ......................... 435/6; 435/91.1; 435/91.2; 435/283.1; 435/287.2; 435/287.9; 536/23.1; 536/24.3; 536/25.3; 502/87; 502/132; 502/309

(58) Field of Classification Search ................ 502/132, 502/309, 87; 435/91.1, 91.2, 6, 287.2, 287.9, 435/283.1; 935/77, 78; 536/24.3, 23.1, 536/25.3
See application file for complete search history.

(56) References Cited

U.S. PATENT DOCUMENTS

| 5,332,629 | A | * | 7/1994 | Sumiya et al. | |
| 5,620,857 | A | * | 4/1997 | Weetall et al. | 435/7.1 |
| 5,641,658 | A | * | 6/1997 | Adams et al. | 435/91.2 |
| 5,688,642 | A | * | 11/1997 | Chrisey et al. | 435/6 |
| 5,777,372 | A | * | 7/1998 | Kobashi | |
| 5,800,992 | A | * | 9/1998 | Fodor et al. | |
| 5,827,637 | A | * | 10/1998 | Uchida et al. | 430/505 |
| 5,965,252 | A | * | 10/1999 | Santo et al. | 428/32.36 |
| 6,133,436 | A | * | 10/2000 | Koster et al. | 536/24.3 |
| 6,607,908 | B1 | * | 8/2003 | Tanga et al. | 435/287.2 |

FOREIGN PATENT DOCUMENTS

JP 09099932 A * 4/1997

OTHER PUBLICATIONS

Lamture et al. Direct Detection of Nucleic Acid Hybridization on the Surface of a Charge Coupled Device. Nucleic Acids Research. vol. 22, No. 11, pp. 2121-2125, Dec. 1994.*
Zhang et al. Single-base mutational analysis of cancer and genetic diseases using membrane bound modified oligonucleotides. Nucleic Acids Research, vol. 19, No. 14, pp. 3929-3933, Dec. 1991.*
Nikifirov et al. The Use of 96-Well Polystyrene plates for DNA-hybridization-based Assays: Analytical Biochemistry, vol. 227, pp. 201-209, May 1995.*
Ninth New Collegiate Dictionary, Merriam-Webster, Springfield Mass., 1991, pp. 357 and 1075.*
Lamture, J. et al., "Direct Detection of Nucleic Acid Hybridization on the Surface of a Charge Coupled Device," Nucleic Acids Research (1994), vol. 22, No. 11, p. 2121-2125.
Eggers et al., "A Microchip for Quantative Detection of Molecules Utilizing Luminescent and Radioisotope Reporter Groups", Biotechniques (1994), vol. 17, No. 3, p. 516-525.

* cited by examiner

*Primary Examiner*—BJ Forman
(74) *Attorney, Agent, or Firm*—Browdy and Neimark, P.L.L.C.

(57) ABSTRACT

Substrates for producing a DNA library are produced by immobilizing DNA onto a suitable substrate having excellent thermal conductivity. A surface of the substrate is chemically modified with a radical having a terminal polar radical. DNA can be amplified by the PCR method in a short period of time using substrates of the present invention onto which DNA is immobilized.

13 Claims, No Drawings

SUBSTRATES FOR IMMOBILIZING AND AMPLIFYING DNA AND DNA-IMMOBILIZED CHIPS

CROSS REFERENCE TO RELATED APPLICATION

The present application is the national stage under 35 U.S.C. 371 of PCT/JP99/00524, filed Feb. 8, 1999.

FIELD OF THE INVENTION

The present invention relates to a substrate for immobilizing DNA, peptides, and the like, particularly to substrates with excellent heat conductivity and which have been chemically modified with a hydroxyl group, a carboxyl group, an epoxy group, and amino group, etc., at a terminal end of the substrates. The present invention also relates to chips having DNA immobilized thereon.

BACKGROUND OF THE INVENTION

Previously, in order to obtain a specific amount of DNA, the DNA was subjected to a polymerase chain reaction (PCR), which involved repeating a number of steps. In a PCR the temperature of a test piece is increased to 95° C. for breaking the hydrogen bond of double DNA chains;

the temperature of the test piece is decreased to 45° C. for binding with a primer in order to reproduce the DNA; and the temperature of the test piece is increased to 74° C. to reproduce DNA by extending the primer using heat-resistant polymerase.

In such a DNA amplifying reaction, a test piece with reaction solution is contained in a tube-shaped plastic reaction container. The container is generally placed into an aluminum block, and the above-noted heat cycles are repeated.

However, because the reaction solution is repeatedly heated and cooled, a long time is required to obtain a specific amount of DNA. In addition, the thermal accuracy for controlling the temperature of the reaction solution is low, so that DNA other than the target DNA may be reproduced.

To resolve the above drawbacks, the present invention provides a solid-state substrate for easily immobilizing DNA and reproducing DNA in accordance with a DNA amplifying reaction, as well as chips having DNA immobilized thereon, and a method for amplifying DNA.

SUMMARY OF THE INVENTION

The substrates of the present invention have excellent thermal conductivity for immobilizing and amplifying DNA. These substrates are preferably diamond or chemically modified diamond. The diamond substrates are preferably modified with a polar group, a carboxyl group, an epoxy group, or an amino group at a terminal end of the substrates.

It is preferable that the carboxyl group be connected to a surface of the substrate through an ester bond or a peptide (amide) bond. The carboxyl group, the epoxy group, or the amino group is connected to a surface of the substrate with a silane coupling agent.

The chips on which DNA is immobilized according to the present invention can be used for amplifying DNA.

DETAILED DESCRIPTION OF THE INVENTION

The substrate of the present invention is a solid state substrate which preferably has excellent thermal conductivity. For example, diamond has one of the best thermal conductivities of all materials, so that diamond can be heated and cooled rapidly. By providing the substrates according to the present invention, the length of time for repeatedly heating and cooling a reaction such as a DNA amplification reaction can be shortened.

In substrates according to the present invention, hydroxyl groups, carboxyl groups, epoxy groups, amino groups, and so on are chemically modified at a surface of the substrate. The DNA and other molecules are easily immobilized so that the substrates according to the present invention are suitable for replicating DNA by a DNA amplification reaction.

In the event that a surface of the substrate is contaminated, chips according to the present invention can replicate chemical modification by hydrolyzing.

In the substrates according to the present invention, the thermal conductivity ratio of a solid-state substrate is preferably at least 0.1 W/cm° K. More preferably, the thermal conductivity ratio is at least 0.5 W/cm° K. Even more preferably, the thermal conductivity ratio is at least 1 W/cm° K. If the thermal conductivity ratio of the substrate is at least 0.1 W/cm° K, heating and cooling can be smoothly alternated in the polymerase chain reaction for amplifying DNA.

Examples of materials having good thermal conductivity are diamond; metals such as silver, copper, aluminum, tungsten, molybdenum, etc; ceramics such as alumina, aluminum nitride, titanium carbide, silicon carbide, and silica. Materials mixed with the above-described materials and ceramic can also be used. Further, plastic materials such as polycarbonate and fluorine resins are suitable. If a material is chemically suitable, the other materials may be suitable in addition to the above-described diamond, metal, ceramics, and plastic. For example, diamond and diamond-like materials can be used. Materials mixed with plastic and the above-described metal, ceramic, and diamond can be used.

For a substrate according to the present invention, diamond, synthetic diamond, high pressurized synthetic diamond, or natural diamond can be used. These kinds of diamonds may be monocrystalline or polycrystalline. In view of productivity, diamond produced by a vapor phase composite method such as a microwave plasma chemical vapor deposition (CVD) method is preferable.

A number of methods for forming a substrate according to the present invention can be used. Examples of these methods include a microwave plasma CVD method, an electron cyclotron resonance chemical vapor deposition (ECRCVD) method, a high frequency plasma CVD method, an inductively coupled plasma (ICP), a direct current (DC) sputtering method, an electron beam (EB) deposition method, and a heat resistant deposition method.

Substrates can also be prepared by mixing metal powder, ceramic powder, or other suitable material with a binder such as a resin. Alternatively, metal powder, ceramic powder, or other material can be pressurized in a press forming machine and the pressurized material sintered at a high temperature.

It is preferable that the surface of a substrate according to the present invention be roughened. Such a surface is suitable for immobilizing a large amount of DNA, since the area of the roughened surface is larger than a smooth surface. The shape of the substrate is not restricted, and the shape can be a plate shape, a thread shape, a ball shape, a polygon shape, a powder shape, etc. Further, a composite type with these substrates and other materials such as double layered materials can be used.

The surface of the substrate is chemically modified, preferably by a polar groups, such as a hydroxyl group, a carboxyl group. That is, a specific group is added to the surface of the substrate to form a chemically modified substrate. By providing such chemical modification, the DNA is easily immobilized onto the surface of the substrate. The polar group can be a hydroxyl group, a carboxyl group, a sulfuric group, a cyano group, a nitro group, a thiol group, an amino group, an epoxy group, and the like. In the above described groups, carboxyl groups may be directly added to a substrate such as diamond or indirectly added to a substrate through another hydroxyl group at a terminal.

Hydroxyl groups having from 1 to 10 carbons are preferable for immobilizing DNA to the substrates of the present invention. Acids for chaining to the hydrocarbon radical can include monocarboxylic acids such as formic acid, acetic acid, and propionic acid; dicarboxylic acids such as oxalic acid, malonic acid, succinic acid, maleic acid, fumaric acid, phthalic acid; and polycarboxylic acids such as trimellitic acid can be used.

For use as a substrate for a DNA amplification reaction by PCR, there are two embodiments. In the first embodiment an anti-hydrolysis characteristic is required, and in a second embodiment chemical modification is reproduced by hydrolysis.

In the embodiment requiring the anti-hydrolysis characteristic, it is preferable that a radical in which a carboxyl radical is connected to a terminal of the hydrolysis radical is connected to a surface of a substrate through a peptide (amide) linkage so as to provide an anti-alkaline characteristic. In the second embodiment, in the case of removing produced chemical modification by hydrolysis and reproduction, it is preferable that a radical in which a carboxyl radical is connected to a terminal of the above hydrolysis radical is connected to a surface of a substrate through an ester linkage so as to provide hydrolysis characteristic in alkaline solution.

To link a hydroxyl radical connected to a terminal of a hydrocarbon radical to a substrate, the surface of the substrate can be oxidized by oxygen plasma and then steaming. The surface of the substrate can be chloridized by irradiating ultraviolet light in chlorine gas and then hydroxylating in alkaline solution. Alternatively, the surface of the substrate is oxidized with oxygen plasma, chloridized, and then hydroxylated in alkaline solution.

To link a hydroxyl radical to a surface of the substrate, chemical modification with a carboxyl radical etc. is strengthened by treatment with a silane coupling agent, a titanium coupling agent, or an aluminum coupling agent.

To connect a carboxyl radical connected to a terminal of a hydrocarbon radical to the substrate through a peptide (amide) linkage, the surface is chloridized by irradiating the substrate with ultraviolet radiation in chlorine gas, amidating the radical by irradiation with ultraviolet radiation in ammonia gas, reaction with carbonic chloride in a nonaqueous solvent, and then neutralizing the radical in alkaline solution.

To link carboxyl radical connected to a terminal of a hydrocarbon radical to the substrate through an ester linkage, the surface is chloridized by irradiating the substrate with ultraviolet radiation in chlorine gas, reacting the surface with sodium carbonate in a nonaqueous solvent, and the neutralizing the substrate with a weak acid solution. Alternatively, the surface of the substrate is oxidized with oxygen plasma, chloridized, hydrolyzed in alkali solution, reacted with carbonic chloride in a nonaqueous solvent, and then neutralizing the substrate in alkaline solution.

Embodiments of the present invention are described in detail hereinafter.

EXAMPLE 1

A vapor phase synthetic diamond of diameter 64 mm and 0.3 mm thickness is produced by a microwave plasma CVD method. The diamond is then polished to have a uniform thickness of 0.25 mm. With respect to a polished surface of 10 mm×10 mm, absorption strength of 2879 $cm^{-1}$, which results from the stretching vibration of carbon and hydrogen is measured by the Fourier transform infrared spectroscopic (FTIR) method. Several pieces of 10 mm×10 mm are cut from the diamond by a laser beam. Each piece is used as a test piece in examples 1 to 6. In Example 1, the surface of the diamond is oxidized with oxygen plasma energized by microwave. Then, the test piece is placed into a separable flask and the air in the seperable flask is replaced with steam. While the steam is in the flask, the flask is heated to 400° C. for 30 minutes, and then cooled.

After the piece in the separable flask is picked up and dried, the piece is a diamond having a hydroxyl radical at a terminal. After the surface of the diamond has been polished, the peak strength of the hydroxyl radical is measured by a secondary ion mass analysis (SIMS) method. Upon comparing with a peak strength of hydrogen as 1, the peak strength of the hydroxyl radical is shown in Table 1.

TABLE 1

| Process | Peak Strength of Hydroxyl Radical |
|---|---|
| After surface polishing | 0.14 |
| After oxygen plasma treatment | 0.70 |
| After steam treatment | 1.14 |

As shown in Table 1, the peak strength of the hydroxyl radical is increased by both the oxygen plasma treatment and the steam treatment. As a result, it is recognized that the surface of the diamond is chemically modified with hydroxyl radical.

EXAMPLE 2

The surface of a vapor phase synthetic diamond as obtained in Example 1 is polished and a test piece of 10 mm×10 mm is cut off by a laser beam. The test piece was sent into a separable flask, and the air in the separable flask was replaced with argon gas. The surface of the diamond was chloridized with chlorine gas having a flow rate of 1 standard cubic centimeter (SCCM) under irradiation by an ultraviolet beam from a Hg—Xe lamp having a main wavelength of 3600 A for 60 minutes. After the air in the flask was replaced by argon gas, the test piece was picked up. The test piece was boiled in a 10 wt % sodium hydroxide solution for 15 minutes and then cleaned and dried to obtain a diamond having a hydroxyl radical at the terminal. After the surface of the diamond was polished and the diamond chloridized by the SIMS method, the peak strengths of hydrogen, hydroxyl radical and the chloride radical were measured, respectively. In the case that the peak strength of hydrogen is 1, each measured peak strength of hydroxyl radical and chloride radical are shown in Table 2.

TABLE 2

| Process | Ratio of peak strength | |
|---|---|---|
| | Hydroxyl radical | Chloride radical |
| After surface polishing | 0.14 | — |
| After chloridizing | 0.20 | 0.50 |
| After sodium hydroxide treatment | 0.47 | 0.35 |

As shown in Table 2, the peak strength of the hydroxyl radical was increased by chloridizing and treatment with sodium hydroxide. As a result, it is recognized that the surface of diamond was chemically modified with hydroxyl radical. Judging from the reduction of the chloride radical, it is recognized that the chloride radical was replaced by the hydroxyl radical.

EXAMPLE 3

The surface of a vapor phase synthetic diamond as obtained in Example 1 was polished. A test piece of 10 mm×10 mm was cut off by a laser beam. The surface of the diamond was oxidized with oxygen plasma energized by microwave, the surface of the diamond was chloridized as in Example 2. After the atmosphere in a flask was replaced with argon gas, the test piece was picked up and boiled in 10 wt % aqueous sodium hydroxide for 15 minutes, cleaned, and dried. As a result, a diamond with hydroxyl radical at the terminal was obtained. In accordance with the SIMS method, the surface of the diamond was polished, treated with oxygen plasma, chloridized, and treated with sodium hydroxide. The peak strength of the hydrogen, hydroxyl radical, and chloride radical were measured, respectively. In the case that the peak strength of hydrogen is 1, each measured peak strength of hydroxyl radical and chloride radical is shown in Table 3.

TABLE 3

| Process | Ratio of peak strength | |
|---|---|---|
| | Hydroxyl radical | Chloride radical |
| After surface polishing | 0.14 | — |
| After oxygen plasma treatment | 0.70 | — |
| After chloridizing | 0.21 | 0.47 |
| After sodium hydroxide treatment | 0.54 | 0.33 |

As shown in Table 3, the peak strength of the hydroxyl radical was increased by the oxygen plasma treatment, chloridization, and sodium hydroxide treatment. As a result, it can be seen that the surface of the diamond was chemically modified with the hydroxyl radical. Judging from the reduction in the chloride radical, it is recognized that the chloride radical was replaced by a hydroxyl radical.

EXAMPLE 4

The surface of a vapor phase synthetic diamond obtained in Example 1 was polished, and a test piece of 10 mm×10 mm was cut off by a laser beam. The test piece was introduced into a separable flask and the air in the separable flask was replaced by argon gas. The surface of the diamond was chloridized with chlorine gas of 1 SCCM flow rate under irradiation by an ultraviolet beam from an Hg—Xe lamp having a main wavelength of 3600 A for 60 minutes. After the air in the flask was again replaced by argon gas, 100 mL of 1% sodium sebacate in N,N-dimethyl formamide was added. A condenser was set up in the separable flask for reflux for two hours. After the test piece was picked up, the test piece was cleaned in 1 wt % acetic acid solution, cleaned with acetone, and dried. The resulting diamond had a carboxyl radical connected to a terminal in which sebacic acid was connected to an ester linkage. In accordance with the SIMS method, the surface of the diamond was polished, chloridized, and treated with sodium salt of sebacic acid. The peak strengths of hydrogen, the hydroxyl radical, and the chloride radical were measured respectively. In the case that the peak strength of hydrogen is 1, each measured peak strength of the hydroxyl radical and the chloride radical are shown in Table 4.

TABLE 4

| Process | Ratio of peak strength | |
|---|---|---|
| | Hydroxyl radical | Chloride radical |
| After surface polishing | 0.14 | — |
| After chloridizing | 0.20 | 0.50 |
| After sodium hydroxide treatment | 0.4 | 0.34 |

As shown in Table 4, the peak strength of the hydroxyl radical was increased by chloridizing and with treatment with sodium salt of sebacic acid. In accordance with the FTIR method, the absorption strength resulting from the stretching vibration of carbon and hydrogen and the absorption strength resulting from stretching vibration of carbon and oxygen were measured by the FTIR method. As a result of the above treatment, each absorption strength was increased. The ratio of absorption strength was increased about 30% with respect to the diamond blank. Therefore, it can be seen that the surface of the diamond was chemically modified with a radical in which the carboxyl radical was connected at a terminal of the hydrocarbon radical of sebacic acid. It can also be seen that the chloride radical was replaced by the hydroxyl radical, since the number of chloride radicals decreased.

EXAMPLE 5

The surface of a vapor phase synthetic diamond obtained in Example 1 was polished, and a test piece of 10 mm×10 mm was cut off by a laser beam. The surface of the diamond was oxidized by oxygen plasma energized by microwave, and the surface of the diamond was chloridized in a manner similar to that shown in Example 2. After replacing the air in a flask with argon gas, the test piece was picked up. The test piece was boiled 10 wt % in potassium hydroxide solution for 15 minutes so as to modify the surface of the diamond with hydroxyl radical. After being dried, the test piece was introduced into a separable flask in which a condenser with a calcium chloride dry pipe at an upper portion thereof was arranged. Fifty mL chloroform and 1 g triethylamine were added, and the atmosphere in the flask was replaced with argon gas. While the separable flask was cooled with ice, a solution of 50 mL chloroform and 10 g succinyl chloride was gradually added. After four hours of refluxing, the test piece was removed, cleaned with 10 wt % potassium carbonate solution, and then dried. The resulting substrate was a diamond with malonic acid connected through an ester linkage, the terminal end of which was connected to a carboxyl radical. In accordance with the SIMS method, the surface of the diamond, which was polished, treated with oxygen plasma, chloridized, hydroxylated, and treated with succinyl chloride was measured for peak strength of hydrogen and hydroxyl radical. In the case that the peak strength of hydrogen is 1, the measured peak strength of the hydroxyl radical is shown in Table 5.

TABLE 5

| Process | Ratio of peak strength of Hydroxyl radical |
| --- | --- |
| After surface polishing | 0.14 |
| After oxygen plasma treatment | 0.70 |
| After chloridizing | 0.21 |
| After hydroxylating | 0.70 |
| After succinyl chloride treatment | 0.50 |

As shown in Table 5, the peak strength of the hydroxyl radical was increased by the oxygen plasma treatment, chloridizing, hydroxylation, and succinyl chloride treatment. In accordance with an FTIR method, the absorption strength resulting from the stretching vibration of carbon and hydrogen and the absorption strength resulting from the stretching vibration of carbon and oxygen were measured. As a result, each absorption strength was increased, .e., the increasing ratio of absorption strength with respect to the diamond blank was about 25%.

Thus, it can be seen that the surface of a diamond was chemically modified with a radical in which the carboxyl radical was connected at a terminal end of the hydrocarbon radical of malonic acid.

EXAMPLE 6

The surface of a vapor phase synthetic diamond obtained in Example 1 was polished, and a test piece of 10 mm×10 mm was cut off by a laser beam. The surface of the diamond was oxidized by oxygen plasma energized by microwave, and the surface of the diamond was chloridized in a manner similar to the method shown in Example 2.

The atmosphere in a separable flask into which the test piece was introduced was replaced by argon gas. While ammonia gas having a flow rate of 1 SCCM was introduced into the flask, the surface of the diamond was modified with amino acid by irradiating with an ultraviolet beam produced by an Hg—Xe lamp having a main wavelength of 3600 A for 60 minutes. After the air in the flask had been replaced by argon gas, a condenser with a calcium chloride dry pipe at the upper end of the condenser was provided. Fifty mL chloroform was added to the flask, and the atmosphere in the flask was replaced by argon gas.

While the separable flask was cooed in ice blocks, 10 g of succinyl chloride in 50 mL chloroform was gradually added. After four hours of reflux the test piece was removed from eh flask. The test piece was cleaned with 10 wt % potassium carbonate solution, rinsed with acetone and dried. The resulting diamond was connected with malonic acid through a peptide linkage connected to a carboxyl radical. In accordance with the SIMS method, the peak strengths of hydrogen, hydroxyl radical, and chloride radical were measured before each treatment, respectively. In the case that the peak strength of hydrogen is 1, each measured peak strength of the hydroxyl radical and the chloride radical are shown in Table 6.

TABLE 6

| | Ratio of peak strength | |
| --- | --- | --- |
| Process | Hydroxyl radical | Chloride radical |
| After hydrogen plasma treatment | 0.06 | — |
| After chloridizing | 0.21 | 0.47 |
| After amino treatment | 0.18 | 0.10 |
| After succinyl chloride treatment | 0.58 | 0.10 |

As shown in Table 6, the peak strength of the hydroxyl radical was increased by the hydrogen plasma treatment chloridizing, hydroxylating, and the succinyl chloride treatment. In accordance with an FTIR method, the absorption strength resulting from the stretching vibration of carbon and hydrogen and the absorption strength resulting from the stretching vibration of carbon and oxygen were measured. It was found that each absorption strength was increased with respect to the diamond blank by 25%. Therefore, it can be seen that the surface of the diamond was chemically modified with a radical in which the carboxyl radical was connected at a terminal of the hydrocarbon radical of malonic acid. Diamonds which have been chemically modified as in examples 1–6 can be used for DNA amplification reactions. After conducting the PCR reaction for one hour, a predetermined amount of DNA can be obtained.

Regarding the diamond chip chemically modified according to the present invention, a terminal chloride radical of oligo nucleic acid may be immobilized at a terminal hydroxyl radical or a terminal carboxyl radical with a hydrogen bond. The oligo nucleic acid and the complementary DNA can be immobilized for use as a DNA library chip. Alternatively, a library chip may be formed by immobilizing nucleotides, oligonucleotides, DNA fragments, etc. on a diamond surface.

EXAMPLE 7

A circular board of titanium carbide of 64 mm diameter, 0.1 mm thickness and surface roughness RA=0.1 mm, was vapor phase synthesized by a high frequency plasma CVD method. A test piece of 3 mm×5 mm was cut from the circular board by a laser beam. The thermal conductivity ratio was 0.44 W/cm° K.

The surface of the test piece was oxidized with oxygen plasma energized by high frequency. The test piece was then introduced into a separable flask. After the air in the flask was replaced by steam, the flask was heated to 400° C. for 30 minutes while steam was introduced into the flask. The flask was left to cool. The test piece was picked up and dried. The test piece was found to be a substrate having a terminal having a hydroxyl radical. The surface of the substrate was then dipped into a silane coupling solution to obtain a substrate covered with a silane coupling agent. The substrate was directly contacted with, a Peltier element as a heating/cooling means so as to thermally control the substrate. Then, the following PCR was conducted.

DNA Immobilization

In the case of messenger RNA (mRNA), oligo-dT16-20 was immobilized on a surface of the substrate. For genomic DNA (gDNA), an oligonucleotide having a target limit enzyme portion was immobilized by chemical ester linkage reaction. For immobilizing complementary DNA (cDNA), mRNA and immobilized oligo-dT16-20 was hybridized with all RNA solution extracted from tissues and cells at a low temperature, i.e., from 0–4° C. The temperature of the substrate was then raised to 37 to 60° C., and cDNA was synthesized by reverse transcriptase (RT) enzyme. In this case cDNA was immobilized by extending toward the 5' of immobilized oligo-dT16-20.

The solution of synthesized immobilized cDNA and mRNA in hybridized condition was heated to 90° C. so as to dehybridize mRNA and the reaction solution was replaced by tris-ethylene diamine tetraacetic acid (tris-EDTA or TE) buffer solution. The substrate was again cooled to between 0 and 4° C., and cleaned with ethanol. The result was a single chain of refined immobilized cDNA on the chip.

gDNA was immobilized in a similar manner. Oligo-deoxythumidylic acid (oligo-dT16-20) immobilized oligo-nucleotide having a target limit enzyme portion was immobilized on a surface of a substrate according to the present invention. Next, reaction solution for chemical immobilization was replaced by a reaction solution including hybrid side oligonucleotide and a right restriction enzyme at a low temperature, i.e, from 0 to 4° C. After hybridization between each oligonucleotide, the substrate was heated to 37° C. so as to cleave the semi-solidified restriction enzyme of the oligonucleotide. After cleaving the restriction enzyme, the temperature of the substrate was lowered to 0–4° C. The solution was replaced by a reaction solution including a cut piece of gDNA with a right restriction enzyme and ligase enzyme. The temperature of the substrate was again increased to 37° C. so as to enable the ligase reaction. Thus, a single chain of gDNA was immobilized on a chip.

The chips containing immobilized cDNA and immobilized gDNA as produced above can be placed into separate containers depending upon their ultimate use, including:
1. comparison of genetic variations of the same kinds of tissues and cells for a plurality of test pieces
2. comparison of the occurrence and changes in genes of each tissue and cell line of the same test piece; and
3. comparison of the occurrence and change of the gene in the same test piece after medical treatment and surgery.

For example, in the case of (1), in order to compare genetic variations of the same kinds of tissues and cells, a plurality of test pieces, i.e., a plurality of DNA immobilized chips) are set in different containers, respectively. These plurality of containers are connected as in one cassette. The cassettes are embedded in the body of a reactor. If at least two cassettes are systematically produced, the test pieces can be effectively compared. To produce a DNA library, one cassette in which a plurality of containers are connected or a plurality of cassettes is designated one aggregation, and a DNA immobilized chip is introduced into each container in the aggregation.

By using these cassette type DNA libraries, the above-described comparisons (1) and (2) can be systematically operated so that genetic changes can be effectively searched. After the chips containing immobilized DNA are sufficiently cleaned in TE buffer solution and 70–75% ethanol solution, the chips are dampened in 100% ethanol and preferred in a frozen condition. Thus the libraries can be used over a period of time in response to the need for comparison data.

Amplifying DNA with Chips Having DNA Immobilized Thereon

A reaction container was formed using a plurality of chips having cDNA immobilized thereon as described above. The reaction container was connected to heating/cooling means under control. The inner surface of the reaction container was sufficiently cleaned with TE buffer solution, a primer with respect to amplifying target DNA was set, and a PCR reaction solution including four kinds of nucleotides and DNA polymerase was added. The temperature of the reaction container was momentarily increased to a thermal metamorphism temperature of 95° C. so as to separate a double chained DNA into a single chain. The container was maintained at a temperature of 95° C. for about 1.5 minute. Then, the container was momentarily cooled to an annealing temperature of 45° C. for connecting the single chain DNA and a DNA primer. The container was maintained at 45° C. for about one minute. Then, the temperature of the container was increased to a DNA amplifying temperature of 75° C. for extending the DNA chain by heat resistant DNA polymerase. The temperature of the container was maintained at 74° C. for about two minutes. The above thermal cycle was repeated 30 times to conduct the polymerase chain reaction. The total time period of the PCR is the sum of the holding periods, or about 135 minutes, since little or no time was needed to bring the reaction container to the proper temperature.

EXAMPLE 8

Vapor phase synthetic diamond as obtained in Example 1 was cut by a laser beam into a test piece of 10 mm×10 mm. The surface of the test piece was treated with hydrogen plasma energized by microwave plasma, in a manner similar to that of Example 2. The surface of the test piece was then chloridized. The air in the container was replaced by argon gas, the test piece was inserted into the container and boiled in potassium hydroxide solution of 10 wt % for fifteen minutes for hydroxylation. The hydroxylated diamond was then immersed in 100 mL of 95% ethanol pH controlled to pH 5 by addition of acetic acid, and 2 mL of 3-hydroxypropylrutrimethoxyl was added with stirring. The treated diamond was removed from the solution and lightly cleaned with ethanol so that an epoxy radical was introduced to a surface of the diamond by treating at 100° C. for five minutes.

EXAMPLE 9

A 5'-terminal amination oligo nucleic acid primer was immobilized on the epoxy radical containing chip prepared as in Example 8. After annealing mRNA, cDNA replica was produced by reverse transcriptase enzyme.

EXAMPLE 10

A vapor phase synthetic diamond as obtained in Example 1 was cut into a 10 mm×10 mm test piece by a laser beam. The surface of the test piece was surface treated by hydrogen plasma energized by microwave plasma, similar to Example 2, and the surface of the diamond was chloridized. The air was replaced by argon gas, and the test piece was boiled in 10 wt % potassium hydroxide solution for 15 minutes to hydroxylate the surface of the diamond. Next, 100 mL of 2 mL 3-aminopropyltrimethoxysilane in 95% ethanol was added to the diamond with stirring. The treated diamond was removed from the solution and lightly cleaned with ethanol so that an amino radical was introduced to the surface of the diamond by treatment at 110° C. for five minutes.

EXAMPLE 11

An oligonucleic acid modified by a carboxyl radical at the 5'-terminal was immobilized on the surface of the diamond prepared as in Example 10 using a peptide linkage. Then, cDNA was immobilized on the diamond by reverse transcriptase while mRNA was used as a casting mold.

EXAMPLE 12

An aluminum nitride circular board of 64 mm diameter and 0.1 mm thickness, surface roughness Ra 0.3 mm was vapor synthesized by an arc ion plating method. A test piece of 3 mm×5 mm was cut from the circular board by a laser beam. The thermal conductivity ratio of 1.70 W/cm° K was obtained. The test piece was introduced into a separable flask and the air in the flask was replaced by argon gas. Chlorine gas was introduced into the flask at 1 SCCM, and the surface of the test piece was chloridized by irradiating ultraviolet light having a main wavelength of 3600 A for 60 minutes onto the test piece. The air in the flask was replaced by argon gas and the test piece was boiled in 10 wt % sodium hydroxide solution for 15 minutes, further cleaned with water, and dried. The resulting substrate had a hydroxyl radical at a terminal thereof. Then similar to Example 1, DNA immobilizing and amplification using the PCR method were effected.

EXAMPLE 13

A tungsten circular plate of 64 mm diameter, 0.5 mm thickness and average surface roughness was obtained by a power-sintering method. A test piece of 3 mm×5 mm was cut from eh circular plate. The thermal conductive ratio was 1.67 W/cm° K. The surface of the test piece was chloridized by oxygen plasma energized by microwave. After the air was replaced by argon gas, the test piece was boiled in sodium hydroxide solution for 15 minutes. The test piece was then cleaned with water and dried so that a substrate having a hydroxyl radical at the terminal was obtained. After that, as in Example 1, the substrate was used for DNA immobilization and amplification by the PCR method.

EXAMPLE 14

An aluminum circular plate was produced by a power sintering method. A test piece of 3 mm×5 mm was divided from the circular plate by laser beam. The thermal conductive ratio was 0.3 W/cm° K. The test piece was introduced into a separable flask and the air in the flask was replaced by argon gas. Chlorine gas was introduced into the flask at 1 SCCM and the surface of the test piece was chloridized by irradiating it with an ultraviolet beam having a main wavelength of 3600 A for 60 minutes. The air in the flask was replaced by argon gas, and 100 mL of 1 wt % sodium salt of sebacic acid in N,N-dimethylformaldehyde was added. A condenser was set into the separable flask and the mixture was refluxed for two hours. The test piece was removed form the solution and cleaned with a 1 wt % acetic acid solution. The test piece was cleaned with acetone and dried for producing a substrate with sebacic acid connected through an ester linkage and carboxyl radical at the terminal. Then, in a similar fashion as in Example 1, the substrate was used for DNA immobilization and amplification by the PCR method.

In addition to contacting the container with heating/cooling means such as a thermistor as described above, the substrates and DNA chips according to the present invention may be inserted into a reaction solution in an Open type tube for similar DNA amplification by the conventional PCR method. In this case, the PCR amplification cannot be finished in as short a time as described above. However, the PCR can still be completed in a shorter period of time than the conventional methods for conducting a PCR.

INDUSTRIAL USE

Substrates according to the present invention having excellent thermal conductivity can be used for DNA amplification by the PCR method in an extremely short period of time as compared to conventional PCR methods. By directly contacting the substrates with heating/cooling means, the accuracy of thermal control of the PCR reaction can be improved so that only DNA which is to be amplified is reproduced.

In a substrate according to the present invention, DNA is directly immobilized onto a solid state substrate which excellent thermal conductive ratio so that the PCR can expeditiously be conducted by directly contacting the substrate with heating/cooling means.

In the substrates according to the present invention, a surface of the substrate is chemically modified with a hydroxyl radical, a carboxyl radi8cal, an epoxy radical, or an amino radical. Therefore, DNA is stably immobilized onto the substrates, and these chips are particularly well suited for reproducing DNA by PCR amplification.

In substrates according to the present invention, chemical modification is produced by hydrolysis in the case in which a surface is contaminated. Therefore, expensive DNA chips can be salvaged.

What is claimed is:

1. Solid state substrate adapted and configured for DNA immobilization, said solid state substrate having a thermal conductivity ratio of at least 0.1 W/cmEK suitable for amplifying and immobilizing DNA, wherein the surface of the substrate is modified by a polar radical formed at the surface of the substrate by binding a chloride by irradiating the surface of the substrate with ultraviolet light in an atmosphere of chlorine gas to bind chloride to the substrate, and replacing the chloride by binding a carboxyl radical to the substrate by setting the substrate into a solution containing a sodium sebacate, wherein the sebacyl radical is introduced to the substrate using a titanium or an aluminum coupling agent.

2. A substrate as claimed in claim 1, wherein said substrate is synthetic diamond or diamond-like carbon.

3. The substrate as claimed in claim 1, wherein said polar radical is a sebacyl radical and said sebacyl radical is connected on a surface of said substrate through amide linkage.

4. The solid state substrate according to claim 1 wherein the surface of the substrate is roughened.

5. A solid state substrate having DNA immobilized thereon, wherein said substrate is diamond or diamond like carbon and said substrate is chemically modified by binding a chloride by irradiating the substrate with ultraviolet light in a chlorine gas atmosphere, and then replacing the chloride with a hydroxyl radial by setting the substrate into a boiling alkali solution or steam, or an amino radical by irradiating the substrate with ultraviolet light in an atmosphere ammonia gas, or a sebacyl radical by setting the substrate into a solution containing sodium sebacate and coupling the sebacyl with a titanium or aluminum coupling agent.

6. The substrate having DNA immobilized thereon as claimed in claim 5, wherein said substrate has a sebacyl radical at a terminal through a hydrocarbon having from 1 to 10 carbon atoms on the surface of the substrate.

7. The solid state substrate according to claim 5 wherein the surface of the substrate is roughened.

8. A chip for amplifying and immobilizing DNA wherein the surface of the chip is modified by binding a chloride by irradiating the chip with ultraviolet light in an atmosphere of chlorine gas, and replacing the chloride by a hydroxyl radical by setting the chip into a boiling alkali solution or steam, or an amino-radical by irradiating the chip with ultraviolet light in an atmosphere of ammonia gas, or a sebacyl by setting the chip into a solution containing sodium sebacate and coupling the sebacyl radical with an aluminum or titanium coupling agent.

9. The chip according to claim 8 wherein the surface of the chip is roughened.

10. A substrate having DNA immobilized thereon, said substrate having a surface modified to contain a sebacyl group, wherein said sebacyl radical is connected to the surface through a titanium coupling agent or an aluminum coupling agent.

11. A solid state substrate having DNA immobilized thereon, wherein said substrate is diamond or diamond like carbon and said substrate is chemically modified by binding a chloride by irradiating the substrate with ultraviolet light in a chlorine gas atmosphere, and then replacing the chloride with a hydroxyl radical by setting the substrate into a boiling alkali solution or steam, or an amino radical by irradiating the substrate with ultraviolet light in an atmosphere of ammonia gas, or a sebacyl radical by setting the substrate into a solution containing sodium sebacate and coupling the sebacyl radical with a titanium or aluminum coupling agent;

Wherein said substrate has a sebacyl radical at a terminal through a hydrocarbon having from 1 to 10 carbon atoms on the surface of the substrate and said sebacyl radical is connected on a surface of said substrate through an ester linkage.

12. A solid state substrate having DNA immobilized thereon, wherein said substrate is diamond or diamond like carbon and said substrate is chemically modified by binding a chloride by irradiating the substrate with ultraviolet light in a chlorine gas atmosphere, and then replacing the chloride with a hydroxyl radical by setting the substrate into a boiling alkali solution or steam or an amino radical by irradiating the substrate with ultraviolet light in an atmosphere of ammonia gas, or a sebacyl radical by setting the substrate into a solution containing sodium sebacate and coupling the sebacyl radical with a titanium or aluminum coupling agent;

Wherein said substrate has a sebacyl radical at a terminal through a hydrocarbon having from 1 to 10 carbon atoms on the surface of the substrate and said sebacyl radical is connected on a surface of said substrate through an amide linkage.

13. A solid state substrate having DNA immobilized thereon, wherein said substrate is diamond or diamond like carbon and said substrate is chemically modified by binding a chloride by irradiating the substrate with ultraviolet light in a chlorine gas atmosphere, and then replacing the chloride with a hydroxyl radical by setting the substrate into a boiling alkali solution or steam or an amino radical by irradiating the substrate with ultraviolet light in an atmosphere of ammonia gas, or a sebacyl radical by setting the substrate into a solution containing sodium sebacate and coupling the sebacyl radical with a titanium or aluminum coupling agent;

Wherein the sebacyl radical is connected to a surface of said substrate with a silane coupling agent, a titanium coupling agent, or an aluminum coupling agent.

* * * * *